US012797313B2

(12) United States Patent
Midha et al.

(10) Patent No.: US 12,797,313 B2

(45) Date of Patent: Nov. 17, 2026

(54) ORAL CARE COMPOSITION COMPRISING OPACIFIER

(71) Applicant: The Procter & Gamble Company, Cincinnati, OH (US)

(72) Inventors: Sanjeev Midha, Mason, OH (US); William Michael Glandorf, Mason, OH (US); Todd Alan Merritt, Mason, OH (US); Lauren G. Tighe, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 457 days.

(21) Appl. No.: 18/317,987

(22) Filed: May 16, 2023

(65) Prior Publication Data

US 2023/0372213 A1 Nov. 23, 2023

Related U.S. Application Data

(60) Provisional application No. 63/344,062, filed on May 20, 2022.

(51) Int. Cl.

| | |
|---|---|
| ***A61K 8/24*** | (2006.01) |
| ***A61K 8/19*** | (2006.01) |
| ***A61K 8/21*** | (2006.01) |
| ***A61K 8/25*** | (2006.01) |
| ***A61Q 11/00*** | (2006.01) |

(52) U.S. Cl.

CPC .................. *A61K 8/24* (2013.01); *A61K 8/19* (2013.01); *A61K 8/21* (2013.01); *A61K 8/25* (2013.01); *A61Q 11/00* (2013.01); *A61K 2800/28* (2013.01); *A61K 2800/30* (2013.01)

(58) Field of Classification Search

CPC ... A61K 8/19; A61K 8/25; A61K 8/24; A61K 8/21; A61K 2800/26; A61K 2800/30; A61K 2800/28; A61Q 11/00

See application file for complete search history.

(56) References Cited

U.S. PATENT DOCUMENTS

| | | | | |
|---|---|---|---|---|
| 3,112,247 | A | 11/1963 | Schweizer | |
| 4,601,899 | A | 7/1986 | Stier et al. | |
| 2021/0093551 | A1* | 4/2021 | Baig | A61K 36/185 |
| 2021/0121392 | A1 | 4/2021 | Shi et al. | |
| 2021/0186842 | A1 | 6/2021 | Asirvatham | |

FOREIGN PATENT DOCUMENTS

| | | | | |
|---|---|---|---|---|
| DE | 9404611 | U1 | 5/1994 | |
| EP | 3283046 | B1 * | 7/2020 | A61K 8/19 |
| EP | 3614993 | B1 | 2/2021 | |
| JP | 2009155240 | A * | 7/2009 | |
| TR | 201308235 | A2 * | 1/2015 | |
| WO | 2008006725 | A1 | 1/2008 | |
| WO | 2021209722 | A1 | 10/2021 | |

OTHER PUBLICATIONS

PCT Search Report and Written Opinion for PCT/US2023/022835 dated Sep. 28, 2023, 14 pages.

* cited by examiner

*Primary Examiner* — Lezah Roberts

(74) *Attorney, Agent, or Firm* — John G. Powell

(57) ABSTRACT

Oral care compositions including β-calcium pyrophosphate as an opacifier in place of titanium dioxide and/or zinc oxide. Toothpaste and/or dentifrice compositions including β-calcium pyrophosphate as an opacifying agent. Oral care compositions, such as toothpaste and/or dentifrice compositions including β-calcium pyrophosphate as the sole opacifying agent. Oral care compositions with a suitable opacity without titanium dioxide.

21 Claims, No Drawings

ORAL CARE COMPOSITION COMPRISING OPACIFIER

FIELD OF THE INVENTION

The present invention relates to oral care compositions comprising opacifier. The present invention also relates to opaque oral care compositions, such as toothpaste and/or dentifrice compositions, which are free of titanium dioxide, zinc oxide, and/or combinations thereof. The present invention further relates to oral care compositions, such as toothpaste and/or dentifrice compositions comprising calcium pyrophosphate as an opacifying agent. The present invention further relates to oral care compositions, such as toothpaste and/or dentifrice compositions comprising calcium pyrophosphate as the sole opacifying agent.

BACKGROUND OF THE INVENTION

Typically, toothpaste compositions are formulated as a single-phase aqueous chassis or a single-phase non-aqueous chassis. In many cases, ingredients are added to toothpaste compositions that can result in toothpaste with an unappealing cloudy appearance, which is neither completely translucent nor completely opaque. Thus, traditional opacifiers, which are typically insoluble particles, such as titanium dioxide, are added to the formulation to make the paste composition a consistent opaque and/or white in appearance. However, many consumers have a perception that certain traditional opacifiers, such as titanium dioxide, can be harmful to health due to their particle size or is considered not safe other biological reasons. Titanium dioxide has been banned in European markets in all food products and several regulations are looking at ban of titanium dioxide in personal and health care products.

Thus, there is a need for a toothpaste composition with a suitable opacity without having to introduce traditional opacifiers, such as titanium dioxide. There is additionally a need for a new opacifier for use in oral care compositions.

Additionally, oral care compositions include a variety of components that can interact with each other. Many insoluble compounds that could be used as opacifiers can interact with other components of oral care compositions, such as fluoride and stannous. Thus, there is a need for an opacifier that does not react or is inert in its reactivity with other components of oral care compositions.

SUMMARY OF THE INVENTION

Disclosed herein is a toothpaste composition, such as an opaque toothpaste composition, comprising (a) β-calcium pyrophosphate; and (b) oral care active agent.

Disclosed herein is a toothpaste composition, such as an opaque toothpaste composition, comprising (a) β-calcium pyrophosphate; and (b) fluoride.

Disclosed herein is a toothpaste composition, such as an opaque toothpaste composition, comprising (a) β-calcium pyrophosphate; and (b) tin.

Disclosed herein is a toothpaste composition, such as an opaque toothpaste composition, comprising (a) β-calcium pyrophosphate; and (b) abrasive.

Disclosed herein is a toothpaste composition, such as an opaque toothpaste composition, comprising (a) β-calcium pyrophosphate; and (b) dicarboxylic acid.

Disclosed herein is a toothpaste composition, such as an opaque toothpaste composition, comprising (a) β-calcium pyrophosphate; and (b) polyphosphate.

Disclosed herein is a toothpaste composition, such as an opaque toothpaste composition, comprising (a) β-calcium pyrophosphate; and (b) hops.

Disclosed herein is a toothpaste composition, such as an opaque toothpaste composition, comprising (a) β-calcium pyrophosphate; and (b) peroxide.

Disclosed herein is a toothpaste composition, such as an opaque toothpaste composition, comprising (a) β-calcium pyrophosphate; and (b) other opacifier.

DETAILED DESCRIPTION OF THE INVENTION

The present invention relates to oral care compositions including β-calcium pyrophosphate with a suitable opacity. Many traditional opacifiers are perceived to carry health risks, thus, the present application is directed to the use of β-calcium pyrophosphate as an opacifying agent in place of traditional opacifiers, such as titanium dioxide and/or zinc oxide. Unexpectedly, it has been found that toothpaste including β-calcium pyrophosphate provides a suitable opacity while maintaining acceptable levels of fluoride and stannous ions.

Definitions

The term "oral care composition", as used herein, includes a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces. Add "unit-dose" and/or fibrous composition The term "dentifrice composition", as used herein, includes tooth or subgingival-paste, gel, or liquid formulations unless otherwise specified. The dentifrice composition may be a single-phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

While compositions and methods are described herein in terms of "comprising" various components or steps, the compositions and methods can also "consist essentially of"

or "consist of" the various components or steps, unless stated otherwise.—Should we define consisting essentially of?

All measurements referred to herein are made at about 23° C. (i.e. room temperature) unless otherwise specified.

The oral care compositions, as described herein, comprise (1) boron nitride and/or (3-calcium pyrophosphate and (2) an oral care active agent, such as fluoride, tin, zinc, polyphosphate, dicarboxylic acid, and/or other ingredients disclosed herein. Additionally, the oral care compositions can comprise other optional ingredients, as described below. The section headers below are provided for convenience only. In some cases, a compound can fall within one or more sections. For example, stannous fluoride can be a tin compound and/or a fluoride compound.

Calcium Pyrophosphate

The present invention is directed to oral care compositions, such as toothpaste and/or dentifrice compositions that can comprise calcium pyrophosphate as an opacifying agent.

The present invention is directed to oral care compositions, such as toothpaste and/or dentifrice compositions comprising boron nitride as an opacifying agent. Typically, toothpaste compositions are formulated as a single-phase aqueous chassis or a single-phase non-aqueous chassis. In many cases, ingredients are added to toothpaste compositions that can result in toothpaste with an unappealing cloudy appearance, which is neither completely translucent nor completely opaque. Thus, traditional opacifiers, which are typically insoluble particles, such as titanium dioxide, are added to the formulation to make the paste composition a consistent opaque and/or white in appearance. However, many consumers have a perception that certain traditional opacifiers, such as titanium dioxide, can be harmful to health due to their particle size.

Thus, the present invention can be directed to the use calcium pyrophosphate as an opacifying agent. Calcium pyrophosphate can be added to oral care compositions that include a lower amount of titanium dioxide and/or zinc oxide or boron nitride can be used to completely replace titanium dioxide and/or zinc oxide. Calcium pyrophosphate can also be combined with other opacifying agents, such as boron nitride, bismuth oxychloride, mica, EGDS, sericite, or combinations thereof While not wishing to be bound by theory, it is believed that particular sources of calcium pyrophosphate can be sufficiently compatible with fluoride and/or tin to be used in an oral care composition comprising fluoride and/or tin. Calcium pyrophosphate has at least three polymorphic phases: alpha (α), beta (β), and gamma (γ). It has been unexpectedly found that calcium pyrophosphate with a higher proportion of the β phase are more compatible with fluoride and/or tin while providing a suitable whiteness value. The opaque toothpaste comprising β calcium pyrophosphate can have a whiteness value (*L) of from about 40 to 100, from about 60 to 100, or from about 75 to 100.

The oral care composition can comprise from about 0.001 to about 10%, from about 0.01% to about 5%, or from about 0.1% to about 2%, by weight of the oral care composition, of the β calcium pyrophosphate.

The calcium pyrophosphate can include at least about 30%, at least about 40%, at least about 50%, and/or at least about 75%, by weight of the calcium pyrophosphate, of calcium pyrophosphate in the β phase.

Boron Nitride

The present invention can include oral care compositions, such as toothpaste and/or dentifrice compositions comprising boron nitride as an opacifying agent. Typically, toothpaste compositions are formulated as a single-phase aqueous chassis or a single-phase non-aqueous chassis. In many cases, ingredients are added to toothpaste compositions that can result in toothpaste with an unappealing cloudy appearance, which is neither completely translucent nor completely opaque. Thus, traditional opacifiers, which are typically insoluble particles, such as titanium dioxide, are added to the formulation to make the paste composition a consistent opaque and/or white in appearance. However, many consumers have a perception that certain traditional opacifiers, such as titanium dioxide, can be harmful to health due to their particle size.

Thus, the present invention can include boron nitride as an opacifying agent. Boron nitride can be added to oral care compositions that include a lower amount of titanium dioxide and/or zinc oxide or boron nitride can be used to completely replace titanium dioxide and/or zinc oxide. Boron nitride can also be combined with other opacifying agents, such as calcium pyrophosphate, bismuth oxychloride, mica, EGDS, sericite, or combinations thereof.

Boron nitride can be a compound comprising an equivalent number of boron and nitrogen atoms in a variety of crystalline forms, which are well known to a person of ordinary skill in the art. The boron nitride can be amorphous (a-boron nitride), hexagonal (h-boron nitride), cubic (c-boron nitride), wurtzite (w-boron nitride), and/or combinations thereof.

The boron nitride can also have metal ions, such as sodium, potassium, calcium, tin, zinc, and/or combinations thereof, intercalated between sheets of boron nitride.

The boron nitride can have an average particle size of from about 0.5 microns to about 100 microns, from about 1 micron to about 50 micron, or from about 2 microns or from about 30 microns.

The oral care composition can comprise from about 0.001 to about 10%, from about 0.01% to about 5%, or from about 0.1% to about 2%, by weight of the oral care composition, of the boron nitride.

The oral care composition and/or toothpaste composition comprising boron nitride can have an opacity about the same or greater than an oral care composition and/or toothpaste composition comprising titanium dioxide and/or zinc oxide. The opaque toothpaste comprising boron nitride can have a whiteness value (*L) of from about 40 to 100, from about 60 to 100, or from about 75 to 100.

Additionally, the boron nitride can be inert and/or have minimal interactions with other oral care actives, such as fluoride, tin, zinc, polyphosphate, dicarboxylic acid, peroxide, amino acid, or combinations thereof, and/or abrasives. Each of the oral care active agents are described in greater detail in the following sections.

Oral Care Active Agent

The oral care composition can combine the boron nitride and/or β-calcium pyrophosphate with one or more oral care active agents, including but not limited to fluoride, metal, tin, zinc, dicarboxylic acid, peroxide, amino acid, and/or hops, as further described herein.

Fluoride

The oral care composition can comprise fluoride, which can be provided by a fluoride ion source. The fluoride ion source can comprise one or more fluoride containing compounds, such as stannous fluoride, sodium fluoride, potassium fluoride, amine fluoride, sodium monofluorophosphate, zinc fluoride, and/or mixtures thereof.

The fluoride ion source and the tin ion source can be the same compound, such as for example, stannous fluoride, which can generate tin ions and fluoride ions. Additionally, the fluoride ion source and the tin ion source can be separate compounds, such as when the tin ion source is stannous chloride and the fluoride ion source is sodium monofluorophosphate or sodium fluoride.

The fluoride ion source and the zinc ion source can be the same compound, such as for example, zinc fluoride, which can generate zinc ions and fluoride ions. Additionally, the fluoride ion source and the zinc ion source can be separate compounds, such as when the zinc ion source is zinc phosphate and the fluoride ion source is stannous fluoride.

The fluoride ion source can be essentially free of or free of stannous fluoride. Thus, the oral care composition can comprise sodium fluoride, potassium fluoride, amine fluoride, sodium monofluorophosphate, zinc fluoride, and/or mixtures thereof.

The oral care composition can comprise a fluoride ion source capable of providing from about 50 ppm to about 5000 ppm, and preferably from about 500 ppm to about 3000 ppm of free fluoride ions. To deliver the desired amount of fluoride ions, the fluoride ion source may be present in the oral care composition at an amount of from about 0.0025% to about 5%, from about 0.01% to about 5%, from about 0.2% to about 1%, from about 0.5% to about 1.5%, or from about 0.3% to about 0.6%, by weight of the oral care composition. Alternatively, the oral care composition can comprise less than 0.1%, less than 0.01%, be essentially free of, be substantially free of, or free of a fluoride ion source.

Metal

The oral care composition, as described herein, can comprise metal, which can be provided by a metal ion source comprising one or more metal ions. The metal ion source can comprise or be in addition to the tin ion source and/or the zinc ion source, as described herein. Suitable metal ion sources include compounds with metal ions, such as, but not limited to Sn, Zn, Cu, Mn, Mg, Sr, Ti, Fe, Mo, B, Ba, Ce, Al, In and/or mixtures thereof. The metal ion source can be any compound with a suitable metal and any accompanying ligands and/or anions.

Suitable ligands and/or anions that can be paired with metal ion sources include, but are not limited to acetate, ammonium sulfate, benzoate, bromide, borate, carbonate, chloride, citrate, gluconate, glycerophosphate, hydroxide, iodide, oxalate, oxide, propionate, D-lactate, DL-lactate, orthophosphate, pyrophosphate, sulfate, nitrate, tartrate, and/or mixtures thereof.

The oral care composition can comprise from about 0.01% to about 10%, from about 1% to about 5%, or from about 0.5% to about 15% of metal and/or a metal ion source.

Tin

The oral care composition of the present invention can comprise tin, which can be provided by a tin ion source. The tin ion source can be any suitable compound that can provide tin ions in an oral care composition and/or deliver tin ions to the oral cavity when the oral care composition is applied to the oral cavity. The tin ion source can comprise one or more tin containing compounds, such as stannous fluoride, stannous chloride, stannous bromide, stannous iodide, stannous oxide, stannous oxalate, stannous sulfate, stannous sulfide, stannic fluoride, stannic chloride, stannic bromide, stannic iodide, stannic sulfide, and/or mixtures thereof. The tin ion source can comprise stannous fluoride, stannous chloride, and/or mixture thereof. The tin ion source can also be a fluoride-free tin ion source, such as stannous chloride.

The oral care composition can comprise from about 0.0025% to about 15%, from about 0.01% to about 10%, from about 0.2% to about 1%, from about 0.4% to about 1%, or from about 0.3% to about 0.6%, by weight of the oral care composition, of tin and/or a tin ion source.

Zinc

The oral care composition can comprise zinc, which can be provided by a zinc ion source. The zinc ion source can comprise one or more zinc containing compounds, such as zinc fluoride, zinc lactate, zinc oxide, zinc phosphate, zinc chloride, zinc acetate, zinc hexafluorozirconate, zinc sulfate, zinc tartrate, zinc gluconate, zinc citrate, zinc malate, zinc glycinate, zinc pyrophosphate, zinc metaphosphate, zinc oxalate, and/or zinc carbonate. The zinc ion source can be a fluoride-free zinc ion source, such as zinc phosphate, zinc oxide, and/or zinc citrate.

The zinc and/or zinc ion source may be present in the total oral care composition at an amount of from about 0.01% to about 10%, from about 0.2% to about 1%, from about 0.5% to about 1.5%, or from about 0.3% to about 0.6%, by weight of the dentifrice composition. Alternatively, the oral care composition can be essentially free of, substantially free of, or free of zinc.

Dicarboxylic Acid

The oral care composition and/or polydentate ligand can comprise dicarboxylic acid. The dicarboxylic acid comprises a compound with two carboxylic acid functional groups. The dicarboxylic acid can comprise a compound or salt thereof defined by Formula I.

Formula I

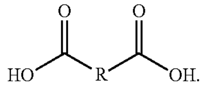

Dicarboxylic acid

R can be null, alkyl, alkenyl, allyl, phenyl, benzyl, aliphatic, aromatic, polyethylene glycol, polymer, O, N, P, and/or combinations thereof.

The dicarboxylic acid can comprise oxalic acid, malonic acid, succinic acid, glutaric acid, adipic acid, pimelic acid, suberic acid, azerlaic acid, sebacic acid, undecanedioic acid, dodecanedioic acid, brassylic acid, thapsic acid, japanic acid, phellogenic acid, equisetolic acid, malic acid, maleic acid, tartaric acid, phthalic acid, methylmalonic acid, dimethylmalonic acid, tartronic acid, mesoxalic acid, dihydroxymalonic acid, fumaric acid, terephthalic acid, glutaric acid, salts thereof, or combinations thereof. The dicarboxylic acid can comprise suitable salts of dicarboxylic acid, such as, for example, monoalkali metal oxalate, dialkali metal oxalate, monopotassium monohydrogen oxalate, dipotassium oxalate, monosodium monohydrogen oxalate, disodium oxalate, titanium oxalate, and/or other metal salts of oxalate. The dicarboxylic acid can also include hydrates of the dicarboxylic acid and/or a hydrate of a salt of the dicarboxylic acid.

The oral care composition can comprise from about 0.01% to about 10%, from about 0.1% to about 15%, from about 1% to about 5%, or from about 0.0001 to about 25%, by weight of the oral care composition, of dicarboxylic acid.

Polyphosphate

The oral care composition can comprise polyphosphate, which can be provided by a polyphosphate source. A polyphosphate source can comprise one or more polyphosphate molecules. Polyphosphates are a class of materials obtained by the dehydration and condensation of orthophosphate to yield linear and cyclic polyphosphates, such as phytic acid, of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21, from about 2 to about 14, or from about 2 to about 7. Alkali earth metal cations, such as calcium, are not preferred because they tend to form insoluble fluoride salts from aqueous solutions comprising a fluoride ions and alkali earth metal cations. Thus, the oral care compositions disclosed herein can be free of or substantially free of calcium pyrophosphate.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass H. Polyphosphates can include those polyphosphate compounds manufactured by FMC Corporation, ICL Performance Products, and/or Astaris.

The oral care composition can comprise from about 0.01% to about 15%, from about 0.1% to about 10%, from about 0.5% to about 5%, from about 1 to about 20%, or about 10% or less, by weight of the oral care composition, of the polyphosphate source. Alternatively, the oral care composition can be essentially free of, substantially free of, or free of polyphosphate. The oral care composition can be essentially free of, substantially free of, or free of cyclic polyphosphate. The oral care composition can be essentially free of, substantially free of, or free of phytic acid, which can lead to insoluble tin and/or zinc compounds.

Surfactants

The oral care composition can comprise one or more surfactants. The surfactants can be used to make the compositions more cosmetically and/or consumer acceptable. The surfactant can be a detersive material which imparts to the composition detersive and foaming properties. Suitable surfactants include anionic, cationic, nonionic, zwitterionic, amphoteric and/or betaine surfactants. Other suitable surfactants include sodium lauryl sulfate, sodium lauryl isethionate, sodium lauroyl methyl isethionate, sodium cocoyl glutamate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine, sodium cocoyl glutamate, and the like. Sodium lauryl sulfate is a preferred surfactant. The oral care composition can comprise one or more surfactants each at a level from about 0.01% to about 15%, from about 0.3% to about 10%, or from about 0.3% to about 2.5%, by weight of the oral care composition.

Thickening Agent

The oral care composition can comprise one or more thickening agents. Thickening agents can be useful in the oral care compositions to provide a gelatinous structure that stabilizes the toothpaste against phase separation. Suitable thickening agents include polysaccharides, polymers, and/or silica thickeners. Some non-limiting examples of polysaccharides include starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof.

The thickening agent can comprise polysaccharides. Polysaccharides that are suitable for use herein include carageenans, gellan gum, locust bean gum, xanthan gum, carbomers, poloxamers, modified cellulose, and mixtures thereof. Carageenan is a polysaccharide derived from seaweed. There are several types of carageenan that may be distinguished by their seaweed source and/or by their degree of and position of sulfation. The thickening agent can comprise kappa carageenans, modified kappa carageenans, iota carageenans, modified iota carageenans, lambda carrageenan, and mixtures thereof. Carageenans suitable for use herein include those commercially available from the FMC Company under the series designation "Viscarin," including but not limited to Viscarin TP 329, Viscarin TP 388, and Viscarin TP 389.

The thickening agent can comprise one or more polymers. The polymer can be a polyethylene glycol (PEG), a polyvinylpyrrolidone (PVP), polyacrylic acid, a polymer derived from at least one acrylic acid monomer, a copolymer of maleic anhydride and methyl vinyl ether, a crosslinked polyacrylic acid polymer, of various weight percentages of the oral care composition as well as various ranges of average molecular ranges. The polymer can comprise polyacrylate crosspolymer, such as polyacrylate crosspolymer-6. Suitable sources of polyacrylate crosspolymer-6 can include Sepimax Zen™ commercially available from Seppic.

The thickening agent can comprise inorganic thickening agents. Some non-limiting examples of suitable inorganic thickening agents include colloidal magnesium aluminum silicate, silica thickeners. Useful silica thickeners include, for example, include, as a non-limiting example, an amorphous precipitated silica such as ZEODENT® 165 silica. Other non-limiting silica thickeners include ZEODENT® 153, 163, and 167, and ZEOFREE® 177 and 265 silica products, all available from Evonik Corporation, and AEROSIL® fumed silicas.

The oral care composition can comprise from 0.01% to about 15%, from 0.1% to about 10%, from about 0.2% to about 5%, or from about 0.5% to about 2% of one or more thickening agents.

Abrasive

The oral care composition of the present invention can comprise abrasive. Abrasives can be added to oral care formulations to help remove surface stains from teeth. The abrasive can comprises calcium abrasive and/or silica abrasive.

The calcium abrasive can be any suitable abrasive compound that can provide calcium ions in an oral care composition and/or deliver calcium ions to the oral cavity when the oral care composition is applied to the oral cavity. The oral care composition can comprise from about 5% to about 70%, from about 10% to about 60%, from about 20% to about 50%, from about 25% to about 40%, or from about 1% to about 50% of a calcium abrasive. The calcium abrasive can comprise one or more calcium abrasive compounds, such as calcium carbonate, precipitated calcium carbonate (PCC), ground calcium carbonate (GCC), chalk, dicalcium phosphate, calcium pyrophosphate, and/or mixtures thereof.

The oral care composition can also comprise silica abrasive, such as silica gel (by itself, and of any structure), precipitated silica, amorphous precipitated silica (by itself, and of any structure as well), hydrated silica, and/or combinations thereof. The oral care composition can comprise from about 5% to about 70%, from about 10% to about 60%, from about 10% to about 50%, from about 20% to about 50%, from about 25% to about 40%, or from about 1% to about 50% of a silica abrasive.

The abrasive can also comprise bentonite, perlite, titanium dioxide, alumina, hydrated alumina, calcined alumina, aluminum silicate, insoluble sodium metaphosphate, insoluble potassium metaphosphate, insoluble magnesium carbonate, zirconium silicate, particulate thermosetting resins and/or other suitable abrasive materials. The oral care composition can comprise from about 5% to about 70%, from about 10% to about 60%, from about 10% to about 50%, from about 20% to about 50%, from about 25% to about 40%, or from about 1% to about 50% of another abrasive.

Amino Acid

The oral care composition can comprise amino acid. The amino acid can comprise one or more amino acids, peptide, and/or polypeptide, as described herein.

Amino acids, as in Formula II, are organic compounds that contain an amine functional group, a carboxyl functional group, and a side chain (R in Formula II) specific to each amino acid. Suitable amino acids include, for example, amino acids with a positive or negative side chain, amino acids with an acidic or basic side chain, amino acids with polar uncharged side chains, amino acids with hydrophobic side chains, and/or combinations thereof. Suitable amino acids also include, for example, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, citrulline, ornithine, creatine, diaminobutanoic acid, diaminoproprionic acid, salts thereof, and/or combinations thereof.

Suitable amino acids include the compounds described by Formula II, either naturally occurring or synthetically derived. The amino acid can be zwitterionic, neutral, positively charged, or negatively charged based on the R group and the environment. The charge of the amino acid, and whether particular functional groups, can interact with tin at particular pH conditions, would be well known to one of ordinary skill in the art.

Formula II

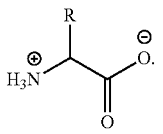

Amino Acid.
R is any suitable functional group

Suitable amino acids include one or more basic amino acids, one or more acidic amino acids, one or more neutral amino acids, or combinations thereof.

The oral care composition can comprise from about 0.01% to about 20%, from about 0.1% to about 10%, from about 0.5% to about 6%, or from about 1% to about 10% of amino acid, by weight of the oral care composition.

The term "neutral amino acid" as used herein includes not only naturally occurring neutral amino acids, such as alanine, asparagine, cysteine, glutamine, glycine, isoleucine, leucine, methionine, phenylalanine, proline, serine, threonine, tryptophan, tyrosine, valine, but also other amino acids having an isoelectric point in range of pH 5.0 to 7.0. The neutral amino acid can also be at least partially water soluble and provide a pH of about 7 or less in an aqueous solution of 1 g of neutral amino acid in 1000 mL of distilled water at 25° C.

Accordingly, suitable neutral amino acids can also include alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, salts thereof, or mixtures thereof. Preferably, neutral amino acids used in the composition of the present invention may include asparagine, glutamine, glycine, salts thereof, and/or mixtures thereof.

Whitening Agent

The oral care composition may comprise from about 0.1% to about 10%, from about 0.2% to about 5%, from about 1% to about 5%, or from about 1% to about 15%, by weight of the oral care composition, of a whitening agent. The whitening agent can be a compound suitable for whitening at least one tooth in the oral cavity. The whitening agent may include peroxides, metal chlorites, perborates, percarbonates, peroxyacids, persulfates, dicarboxylic acids, and combinations thereof. Suitable peroxides include solid peroxides, hydrogen peroxide, urea peroxide, calcium peroxide, benzoyl peroxide, sodium peroxide, barium peroxide, inorganic peroxides, hydroperoxides, organic peroxides, and mixtures thereof. Suitable metal chlorites include calcium chlorite, barium chlorite, magnesium chlorite, lithium chlorite, sodium chlorite, and potassium chlorite. Other suitable whitening agents include sodium persulfate, potassium persulfate, peroxydone, 6-phthalimido peroxy hexanoic acid, Pthalamidoperoxycaproic acid, or mixtures thereof.

Humectant

The oral care composition can comprise one or more humectants, have low levels of humectant, be free of humectant, be substantially free of humectant, and/or essentially free of humectant. Humectants serve to add body or "mouth texture" to an oral care composition or dentifrice as well as preventing the dentifrice from drying out. Suitable humectants include polyethylene glycol (at a variety of different molecular weights), propylene glycol, glycerin (glycerol), erythritol, xylitol, sorbitol, mannitol, butylene glycol, lactitol, hydrogenated starch hydrolysates, and/or mixtures thereof. The oral care composition can comprise one or more humectants each at a level of from 0 to about 70%, from about 5% to about 50%, from about 10% to about 60%, or from about 20% to about 80%, by weight of the oral care composition.

Water

The oral care composition of the present invention can be a dentifrice composition that is anhydrous, a low water formulation, or a high water formulation. In total, the oral care composition can comprise from 0% to about 99%, about 20% or greater, about 30% or greater, about 50% or greater, up to about 45%, or up to about 75%, by weight of the composition, of water. Preferably, the water is USP water.

In a high water dentifrice formulation, the dentifrice composition comprises from about 45% to about 75%, by weight of the composition, of water. The high water dentifrice composition can comprise from about 45% to about 65%, from about 45% to about 55%, or from about 46% to about 54%, by weight of the composition, of water. The water may be added to the high water dentifrice formulation and/or may come into the composition from the inclusion of other ingredients.

In a low water dentifrice formulation, the dentifrice composition comprises from about 10% to about 45%, by weight of the composition, of water. The low water dentifrice composition can comprise from about 10% to about 35%, from about 15% to about 25%, or from about 20% to about 25%, by weight of the composition, of water. The water may be added to the low water dentifrice formulation and/or may come into the composition from the inclusion of other ingredients.

In an anhydrous dentifrice formulation, the dentifrice composition comprises less than about 10%, by weight of the composition, of water. The anhydrous dentifrice composition comprises less than about 5%, less than about 1%, or 0%, by weight of the composition, of water. The water may be added to the anhydrous formulation and/or may come into the dentifrice composition from the inclusion of other ingredients.

The dentifrice composition can also comprise other orally acceptable carrier materials, such as alcohol, humectants, polymers, surfactants, and acceptance improving agents, such as flavoring, sweetening, coloring and/or cooling agents.

The oral care composition can also be a mouth rinse formulation. A mouth rinse formulation can comprise from about 75% to about 99%, from about 75% to about 95%, or from about 80% to about 95% of water.

*Humulus lupulus*

The oral care compositions of the present invention can comprise hops. The hops can comprise at least one hops compound from Formula III and/or Formula VI. The compound from Formula III and/or Formula VI can be provided by any suitable source, such as an extract from *Humulus lupulus* or Hops, *Humulus lupulus* itself, a synthetically derived compound, and/or salts, prodrugs, or other analogs thereof. The hops extract can comprise one or more hops alpha acids, one or more hops iso-alpha acids, one or more hops beta acids, one or more hops oils, one or more flavonoids, one or more solvents, and/or water. Suitable hops alpha acids (generically shown in Formula III) can include humulone (Formula IV), adhumulone, cohumulone, posthumulone, prehumulone, and/or mixtures thereof. Suitable hops iso-alpha acids can include cis-isohumulone and/or trans-isohumulone. The isomerization of humulone into trans-isohumulone can be represented by Formula V.

Formula III

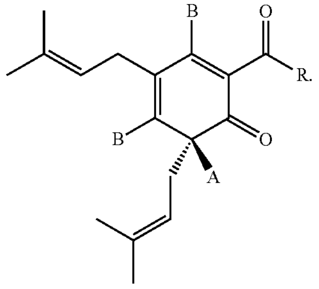

Hops Alpha Acids. A is the acidic hydroxyl functional group in the alpha position, B are the acidic hydroxyl functional groups in the beta position, and R is an alkyl functional group.

Formula IV

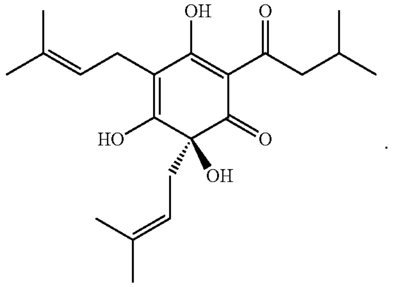

Humulone

Formula V

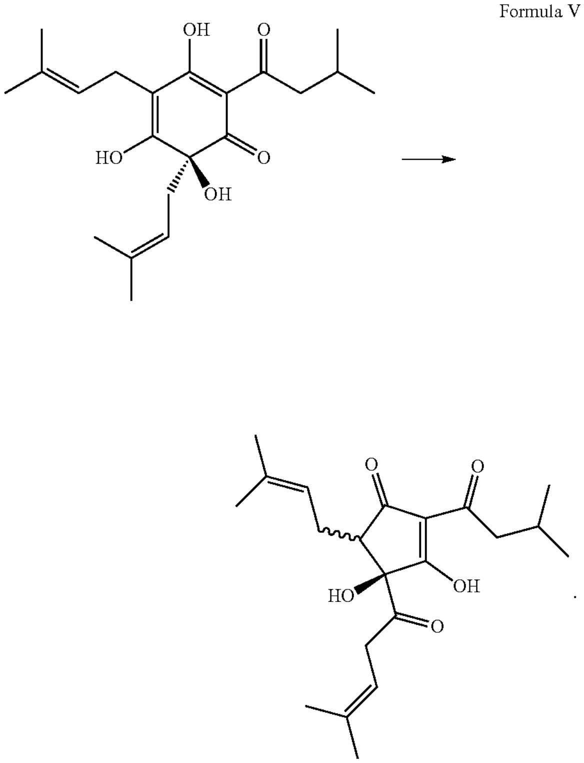

Isomerization of Humulone to isohumulone.

Suitable hops beta acids can include lupulone, adlupulone, colupulone, and/or mixtures thereof. A suitable hops beta acid can include a compound a described in Formula III, VII, VIII, and/or IX.

Formula VI

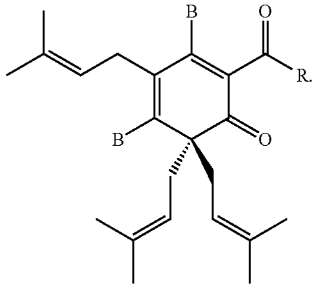

Hops Beta Acids. B are the acidic hydroxyl functional groups in the beta position and R is an alkyl functional group.

Formula VII

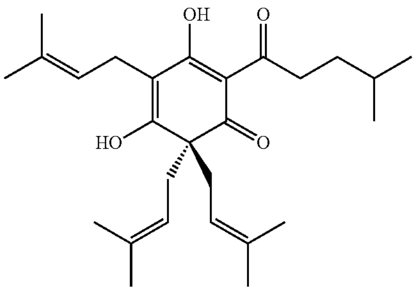

Lupulone

Formula VIII

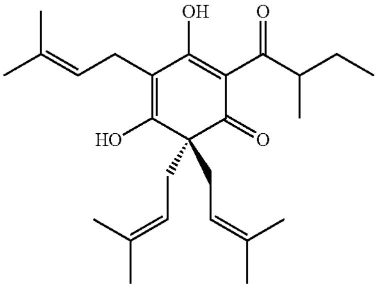

Adlupulone

Formula IX

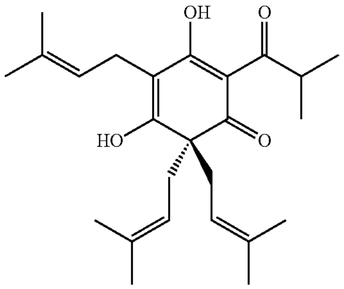

Colupulone

While hops alpha acids can demonstrate some antibacterial activity, hops alpha acids also have a bitter taste. The bitterness provided by hops alpha acids can be suitable for beer, but are not suitable for use in oral care compositions. In contrast, hops beta acids can be associated with a higher antibacterial and/or anticaries activity, but not as bitter a taste. Thus, a hops extract with a higher proportion of beta acids to alpha acids than normally found in nature, can be suitable for use in oral care compositions for use as an antibacterial and/or anticaries agent.

A natural hops source can comprise from about 2% to about 12%, by weight of the hops source, of hops beta acids depending on the variety of hops. Hops extracts used in other contexts, such as in the brewing of beer, can comprise from about 15% to about 35%, by weight of the extract, of hops beta acids. The hops extract desired herein can comprise at least about 35%, at least about 40%, at least about 45%, from about 35% to about 95%, from about 40% to about 90%, or from about 45% to about 99%, of hops beta acids. The hops beta acids can be in an acidic form (i.e. with attached hydrogen atom(s) to the hydroxyl functional group (s)) or as a salt form.

A suitable hops extract is described in detail in U.S. Pat. No. 7,910,140, which is herein incorporated by reference in its entirety. The hops beta acids desired can be non-hydrogenated, partially hydrogenated by a non-naturally occurring chemical reaction, or hydrogenated by a non-naturally occurring chemical reaction. The hops beta acid can be essentially free of or substantially free of hydrogenated hops beta acid and/or hops acid. A non-naturally occurring chemical reaction is a chemical reaction that was conducted with the aid of chemical compound not found within *Humulus lupulus*, such as a chemical hydrogenation reaction conducted with high heat not normally experienced by *Humulus lupulus* in the wild and/or a metal catalyst.

A natural hops source can comprise from about 2% to about 12%, by weight of the hops source, of hops alpha acids. Hops extracts used in other contexts, such as in the brewing of beer, can comprise from about 15% to about 35%, by weight of the extract, of hops alpha acids. The hops extract desired herein can comprise less than about 10%, less than about 5%, less than about 1%, or less than about 0.5%, by weight of the extract, of hops alpha acids.

Hops oils can include terpene hydrocarbons, such as myrcene, humulene, caryophyllene, and/or mixtures thereof. The hops extract desired herein can comprise less than 5%, less than 2.5%, or less than 2%, by weight of the extract, of one or more hops oils.

Flavonoids present in the hops extract can include xanthohumol, 8-prenylnaringenin, isoxanthohumol, and/or mixtures thereof. The hops extract can be substantially free of, essentially free of, free of, or have less than 250 ppm, less than 150 ppm, and/or less than 100 ppm of one or more flavonoids.

As described in U.S. Pat. No. 5,370,863, hops acids have been previously added to oral care compositions. However, the oral care compositions taught by U.S. Pat. No. 5,370,863 only included up to 0.01%, by weight of the oral care composition. While not wishing to be bound by theory, it is believed that U.S. Pat. No. 5,370,863 could only incorporate a low amount of hops acids because of the bitterness of hops alpha acids. A hops extract with a low level of hops alpha acids would not have this concern.

The hops compound can be combined with or free from an extract from another plant, such as a species from genus *Magnolia*. The hops compounds can be combined with or free from triclosan.

The oral care composition can comprise from about 0.01% to about 10%, greater than 0.01% to about 10%, from about 0.05%, to about 10%, from about 0.1% to about 10%, from about 0.2% to about 10%, from about 0.2% to about 10%, from about 0.2% to about 5%, from about 0.25% to about 2%, from about 0.05% to about 2%, or from greater than 0.25% to about 2%, of hops, such as hops beta acid, as described herein. The hops, such as the hops beta acid, can be provided by a suitable hops extract, the hops plant itself, or a synthetically derived compound. The hops, such as hops beta acid, can be provided as neutral, acidic compounds, and/or as salts with a suitable counter ion, such as sodium, potassium, ammonia, or any other suitable counter ion.

The hops can be provided by a hops extract, such as an extract from *Humulus lupulus* with at least 35%, by weight of the extract, of hops beta acid and less than 1%, by weight of the hops extract, of hops alpha acid. The oral care composition can comprise 0.01% to about 10%, greater than 0.01% to about 10%, from about 0.05%, to about 10%, from about 0.1% to about 10%, from about 0.2% to about 10%, from about 0.2% to about 10%, from about 0.2% to about 5%, from about 0.25% to about 2%, from about 0.05% to about 2%, or from greater than 0.25% to about 2%, of hops extract, as described herein.

Other Ingredients

The oral care composition can comprise a variety of other ingredients, such as flavoring agents, sweeteners, colorants, preservatives, buffering agents, or other ingredients suitable for use in oral care compositions, as described below.

Flavoring agents also can be added to the oral care composition. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") or N-(Ethoxycarbonylmethyl)-3-p-menthanecarboxamide (known commercially as "WS-5"), and mixtures thereof. A flavor system is generally used in the compositions at levels of from about 0.001% to about 5%, by weight of the oral care composition. These flavoring agents generally comprise mixtures of aldehydes, ketones, esters, phenols, acids, and aliphatic, aromatic and other alcohols.

Sweeteners can be added to the oral care composition to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, sucralose, stevia, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Preservatives also can be added to the oral care compositions to prevent bacterial growth. Suitable preservatives approved for use in oral compositions such as methylparaben, propylparaben, benzoic acid, and sodium benzoate can be added in safe and effective amounts.

Titanium dioxide and/or zinc oxide may also be added to the present composition. Titanium dioxide is a white powder which adds opacity to the compositions. Alternatively, the oral care composition can be essentially free of, substantially free of, and/or free of titanium dioxide and/or zinc oxide.

Other ingredients can be used in the oral care composition, such as desensitizing agents, healing agents, other caries preventative agents, chelating/sequestering agents, vitamins, proteins, other anti-plaque/anti-calculus agents, opacifiers, antibiotics, anti-enzymes, enzymes, pH control agents, oxidizing agents, antioxidants, and the like.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Opaque Toothpaste Compositions

The control toothpaste and Examples 1-17 were made by combining a toothpaste base (See TABLE 1D for identity of toothpaste base) with one or more potential opacifying agents, silica, and flavor. The control toothpaste did not include any opacifying agents.

Whiteness

The whiteness of the toothpaste compositions described in TABLEs 1-2 (the control toothpaste and Examples 1-17) were determined using the CIE color model. These compositions were evaluated for their L*a*b* color readings using a hand held (portable) Smart Probe 400 colorimeter (IMS Inc.). Portable colorimeter is a color measurement tool for psychophysical analysis, which measures human eye-brain perception. Colorimetric data were directly read and provided as tristimulus values-X,Y,Z. The Lab values were calculated according to the tristimulus values.

A CIE L*a*b* color model (Lab) method was used to quantify toothpaste whiteness. The lightness (whiteness) component (L*) value can range from 0-100. Typically, $TiO_2$ containing toothpastes have L* values close to 90. Desirable compositions disclosed herein included compositions with L* values of from about 40 to 100, from about 60 to 100, from about 75 to 100, at least about 60, or at least about 75 were sufficiently white/opaque for consumer acceptance.

Fluoride Compatibility

Fluoride compatibility was determined by first preparing a stannous fluoride and sodium gluconate stock solution. 0.34 g of stannous fluoride, 0.48 g of sodium gluconate and 74.3 g of water were combined in a polypropylene bottle. The mixture was stirred at room temperature until all solids dissolved. The target fluoride concentration was 1100 μg/g F-.

Next, a 0.2 N EDTA/0.2 N THAM buffer solution was prepared by weighing 74.4 g disodium EDTA into a 1000 mL beaker, adding 24.2 g THAM (2-amino-2-(hydroxymethyl)-1,3-propanediol) and about 800 mL of water. The mixture was stirred until all the solids dissolved. Once the solution equilibrated to room temperature, the pH was adjusted to 7.95-8.05 using 50% w/w NaOH, quantitatively transferred to a 1000 mL volumetric flask, diluted and mixed well.

Fluoride ion working calibration standards were prepared from a 1000 ppm F-standard stock solution by diluting with EDTA/THAM buffer solution for target concentrations of 10, 50 and 100 μg/g of F.

Test compositions were prepared by weighing 3.49-3.51 g of test composition in a sample cup equipped with a cap. 14.95-15.05 g of stannous fluoride/sodium gluconate stock solution was added to the cup and mixed.

Standard compositions were prepared by adding only 14.95-15.05 g of stannous fluoride/sodium gluconate into a sample cup with a cap.

The prepared test compositions and prepared standard compositions were stored at 60° C. while being rotated for two hours. The compositions were removed from storage and centrifuged for 15 minutes at a speed of 25000 RCF. A clear supernatant was identified upon centrifugation. 1.48-1.52 g of the clear supernatant isolated was combined with 13.47-13.53 g of additional EDTA/THAM buffer solution. A pre-calibrated fluoride electrode was placed in the solution and the concentration of fluoride ions was read.

Fluoride compatibility was determined using Formula A, below.

Flouride Compatability

Formula A $$\%\ \text{Compatability} = \frac{[F^{-}]ppm \text{ in Silica sample } x\ 100\%}{\text{measured } [F^{-}]ppm \text{ in } SnF2/NaGluc \text{ Standard}}$$

TABLE 1A

| Toothpaste Compositions | | | | | | | | |
|---|---|---|---|---|---|---|---|---|
| Ingredient | Control | Ex. 1 (wt %) | Ex. 2 (wt %) | Ex. 3 (wt %) | Ex. 4 (wt %) | Ex. 5 (wt %) | Ex. 6 (wt %) | Ex. 7 (wt %) |
| Toothpaste Base[1] | 84 | 81 | 81 | 81 | 79 | 81 | 81 | 83 |
| Silica (Z109) | 16 | 15 | 15 | 15 | 15 | 15 | 15 | 15 |
| Flavor | 1 | 1 | 1 | 1 | 1 | 1 | 1 | 1 |
| Cal Pyro | | 3 | — | — | — | 1 | — | 1 |
| Cal Pyro (High β Phase)[2] | — | — | 3 | — | — | — | 1 | — |
| EGDS[3] | — | — | — | 3 | 5 | 3 | 3 | — |

[1]See TABLE 1D
[2][Insert info on Beta Calpyro];
[3]Hall Star ® EGDS (glycol distearate)

TABLE 1B

| Toothpaste Compositions | | | | | | |
|---|---|---|---|---|---|---|
| Ingredient | Control | Ex. 8 (wt %) | Ex. 9 (wt %) | Ex. 10 (wt %) | Ex. 11 (wt %) | Ex. 12 (wt %) |
| Toothpaste Base[1] | 84 | 83 | 83 | 83 | 83 | 83 |
| Silica (Z109) | 16 | 15 | 15 | 15 | 15 | 15 |
| Flavor | 1 | 1 | 1 | 1 | 1 | 1 |
| Bismuth Oxychloride (PG1086) | — | 1 | — | — | — | — |
| Bismuth Oxychloride (PG1099) | — | — | 1 | — | — | — |
| Kobo Mica Y-08 | — | — | — | 1 | — | — |
| Kobo Mica SM-08 | — | — | — | | 1 | — |
| Sericite GMS-4C | — | — | — | | — | 1 |

[1]See TABLE 1D

TABLE 1C

| Toothpaste Compositions | | | | | | |
|---|---|---|---|---|---|---|
| Ingredient | Control | Ex. 13 (wt %) | Ex. 14 (wt %) | Ex. 15 (wt %) | Ex. 16 (wt %) | Ex. 17 (wt %) |
| Toothpaste Base[1] | 84 | 83 | 83 | 83.9 | 83.75 | 83.5 |
| Silica (Z109) | 16 | 15 | 15 | 15 | 15 | 15 |
| Flavor | 1 | 1 | 1 | 1 | 1 | 1 |
| Boron Nitride[2] (2 μm) | — | 1 | — | 0.1 | 0.25 | 0.5 |
| Boron Nitride[3] (30 μm) | — | — | 1 | — | — | — |

[1]See TABLE 1D
[2]Cress ® BN02;
[3]Cress ® BN30

TABLE 1D

| Toothpaste Base | |
|---|---|
| Ingredient | Amount (% wt) |
| Sorbitol | 55.29 |
| Water | 30.06 |
| $SnCl_2$ 10% silica blend | 0.53 |
| Sodium gluconate | 0.66 |
| NaOH (50%) | 1.53 |
| Saccharin | 1.02 |
| Sucralose | 0.47 |
| Xanthan Gum | 0.24 |
| Carrageenan | 0.82 |
| Sodium Citrate | 1.62 |
| Zinc Citrate | 1.24 |
| Sodium Lauryl Sulfate | 5.88 |

TABLE 2A

| Whiteness of Toothpaste Compositions | | | | |
|---|---|---|---|---|
| | Opacifier | *L | Soluble F Initial (ppm) | Soluble F 30 Days (ppm) |
| Control | None | 57.7 | 929 | 946 |
| Ex. 1 | 3% Cal Pyro | 74.3 | 702 | 589 |
| Ex. 2 | 3% Cal Pyro (β) | 75.7 | 814 | 827 |
| Ex. 3 | 3% EGDS | 69.5 | 901 | 908 |
| Ex. 4 | 5% EGDS | 73.4 | 877 | 899 |
| Ex. 5 | 3% EGDS/1% CalPyro | 74.4 | 827 | 638 |
| Ex. 6 | 3% EGDS/1% CalPyro (β) | 72.7 | 870 | 856 |

TABLE 2A-continued

| Whiteness of Toothpaste Compositions | | | | |
|---|---|---|---|---|
| | Opacifier | *L | Soluble F Initial (ppm) | Soluble F 30 Days (ppm) |
| Ex. 7 | 1% Cal Pyro | 69.0 | — | — |
| Ex. 8 | 1% Bismuth Oxychloride | 75.8 | — | — |
| Ex. 9 | 1% Bismuth Oxychloride | 80.9 | — | — |
| Ex. 10 | 1% Mica | 64.1 | — | — |
| Ex. 11 | 1% Mica | 64.8 | — | — |
| Ex. 12 | 1% Sericite | 63.8 | — | — |
| Ex. 13 | 1% BN (2 μm) | 86.5 | — | — |
| Ex. 14 | 1% BN (30 μm) | 70.8 | — | — |
| Ex. 15 | 0.1% BN (2 μm) | 69.6 | — | — |
| Ex. 16 | 0.25% BN (2 μm) | 78.2 | — | — |
| Ex. 17 | 0.50% BN (2 μm) | 83.0 | — | — |

TABLE 2B

| Fluoride Compatibility | |
|---|---|
| Opacifier | % Fluoride Compatibility |
| Boron nitride 30 μm (Cress ® BN30) | 94.2 |
| Boron nitride 2 μm (Cress ® BN02) | 96.0 |
| Bismuth Oxychloride (Pearl Glo UVR PG 1086) | 97.9 |
| Bismuth Oxychloride (Pearl Glo UVR PG 1099) | 100.8 |
| Sericite (GMS-4C) | 83.5 |
| Mica (Kobo Mica SM-08) | 82.3 |
| Mica (Kobo Mica Y-08) | 53.2 |

Several opacifiers were screened for whiteness in TABLE 2A: calcium pyrophosphate, β-calcium pyrophosphate, EGDS, bismuth oxychloride, sericite, mica, boron nitride, and/or combinations thereof. An initial target *L value of 75 was utilized to screen out ineffective opacifiers. Only boron nitride, calcium pyrophosphate, and bismuth oxychloride were identified to have a high enough whiteness value to be effective in replacing titanium dioxide and/or zinc oxide.

Calcium pyrophosphate (Ex. 1) had a *L of 74.3, but had low soluble fluoride numbers initially (702 ppm) and at 30 days (589 ppm) from a target fluoride amount of 1100 ppm. Thus, calcium pyrophosphate (Ex. 1) was not compatible enough with fluoride to be used as an opacifier in a fluoride-containing toothpaste product.

Calcium pyrophosphate which was primarily in the 3-phase (Ex. 2) had a slightly higher whiteness value of 75.7, but had much higher soluble fluoride numbers initially (814 ppm) and at 30 days (827 ppm) from a target fluoride amount of 1100 ppm. Thus, β-calcium pyrophosphate (Ex. 2) was compatible enough with fluoride to be used as an opacifier in a fluoride-containing toothpaste product.

Bismuth oxychloride (Ex. 8 and Ex. 9) had whiteness values (*L) of 75.8 and 80.9 and high levels of fluoride compatibility (97.9% and 100.8%).

Boron nitride (Ex. 13-17) had whiteness values (*L) of 69.6 to 86.5. At 1% boron nitride (2 μm, Ex. 13) the whiteness value was 86.5. Additionally, boron nitride was unexpectedly stable with fluoride, showing a 94-96% fluoride compatibility depending on the average diameter of the boron nitride particle. Thus, boron nitride unexpectedly provided suitable whiteness and fluoride compatibility such that boron nitride could, alone or in part, replace titanium dioxide and/or zinc oxide as an opacifying agent in toothpaste.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A toothpaste composition comprising:

(a) about 0.01% to about 5%, by weight of the toothpaste composition, of a first opacifier comprising calcium pyrophosphate, wherein at least 75% of the calcium pyrophosphate is β-phase calcium pyrophosphate;

(b) a second opacifier comprising ethylene glycol distearate (EGDS);

(c) fluoride; and (d) an oral care active agent comprising tin, wherein the composition has a whiteness value (L*) of about 75 to 100 and at least 800 ppm of soluble fluoride after 30 days.

2. The toothpaste composition of claim 1, wherein the toothpaste composition is free of zinc citrate, zinc oxide, zinc phosphate, or combinations thereof.

3. The toothpaste composition of claim 1, wherein the toothpaste composition is free of titanium dioxide and/or zinc oxide.

4. The toothpaste composition of claim 1, wherein the toothpaste composition comprises from about 0.01% to about 5%, by weight of the toothpaste composition, of boron nitride.

5. The toothpaste composition of claim 4, wherein the boron nitride comprises amorphous boron nitride, hexagonal boron nitride, cubic boron nitride, wurtzite boron nitride, or combinations thereof.

6. The toothpaste composition of claim 4, wherein the boron nitride comprises particles of boron nitride with an average particle size of from about 1 micron to about 50 microns.

7. The toothpaste composition of claim 4, wherein the boron nitride comprises particles of boron nitride with an average particle size of from about 2 microns to about 30 microns.

8. The toothpaste composition of claim 1, wherein the oral care active agent further comprises zinc, polyphosphate, dicarboxylic acid, peroxide, amino acid, hops, or combinations thereof.

9. The toothpaste composition of claim 1, wherein the fluoride comprises sodium fluoride, stannous fluoride, sodium monofluorophosphate, amine fluoride, or combinations thereof.

10. The toothpaste composition of claim 8, wherein the oral care active agent comprises the hops, and wherein the hops comprises hops beta acid.

11. The toothpaste composition of claim 1, wherein the tin comprises stannous fluoride, stannous chloride, stannous pyrophosphate, or combinations thereof.

12. The toothpaste composition of claim 8, wherein the oral care active agent comprises the zinc, and the zinc comprises zinc lactate, zinc citrate, zinc chloride, zinc phosphate, zinc oxide, or combinations thereof.

13. The toothpaste composition of claim 8, wherein the oral care active agent comprises the polyphosphate, and the polyphosphate comprises a linear polyphosphate having the formula: $XO(XPO_3)_nX$, wherein X is sodium, potassium, ammonium, or any other alkali metal cations and n averages from about 2 to about 21.

14. The toothpaste composition of claim 8, wherein the oral care active agent comprises the polyphosphate, and the polyphosphate comprises pyrophosphate, tripolyphosphate, or hexametaphosphate.

15. The toothpaste composition of claim 8, wherein the oral care active agent further comprises the dicarboxylic acid, and wherein the dicarboxylic acid comprises oxalic acid, malonic acid, succinic acid, glutaric acid, adipic acid, pimelic acid, suberic acid, azerlaic acid, sebacic acid, undecanedioic acid, dodecanedioic acid, brassylic acid, thapsic acid, japanic acid, phellogenic acid, equisetolic acid, malic acid, maleic acid, tartaric acid, phthalic acid, methylmalonic acid, dimethylmalonic acid, tartronic acid, mesoxalic acid, dihydroxymalonic acid, fumaric acid, terephthalic acid, glutaric acid, salts thereof, or combinations thereof.

16. The toothpaste composition of claim 8, wherein the oral care active agent comprises the amino acid, and the amino acid comprises arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, citrulline, ornithine, creatine, diaminobutanoic acid, diaminoproprionic acid, salts thereof, or combinations thereof.

17. The toothpaste composition of claim 16, wherein the amino acid comprises glycine.

18. The toothpaste composition of claim 1, wherein the toothpaste composition comprises abrasive.

19. The toothpaste composition of claim 18, wherein the abrasive comprises silica abrasive, calcium abrasive, or combinations thereof.

20. The toothpaste composition of claim 19, wherein the calcium abrasive comprises calcium pyrophosphate, calcium carbonate, or combinations thereof.

21. The toothpaste composition of claim 1, wherein the EGDS is present at about 3% to 5%, by weight of the toothpaste composition.

* * * * *